United States Patent
Ohler et al.

(10) Patent No.: US 11,136,283 B2
(45) Date of Patent: Oct. 5, 2021

(54) RECOVERING AND PURIFYING RESVERATROL PRODUCED BY MICROBIAL FERMENTATION

(71) Applicant: EVOLVA SA, Reinach (CH)

(72) Inventors: Nicholas Lawrence Ohler, Copenhagen Ø (DK); Satish Kumar Bachu, Copenhagen Ø (DK); Oliver Frankovic, Copenhagen Ø (DK)

(73) Assignee: EVOLVA SA, Reinach (CH)

( * ) Notice: Subject to any disclaimer, the term of this patent is extended or adjusted under 35 U.S.C. 154(b) by 0 days.

(21) Appl. No.: 16/481,943

(22) PCT Filed: Jan. 31, 2018

(86) PCT No.: PCT/EP2018/052412
§ 371 (c)(1),
(2) Date: Jul. 30, 2019

(87) PCT Pub. No.: WO2018/141798
PCT Pub. Date: Aug. 9, 2018

(65) Prior Publication Data
US 2020/0039909 A1 Feb. 6, 2020

(30) Foreign Application Priority Data
Jan. 31, 2017 (GB) ..................... 1701598

(51) Int. Cl.
*C07C 37/84* (2006.01)
*C07C 39/21* (2006.01)
*C12P 7/22* (2006.01)

(52) U.S. Cl.
CPC .............. *C07C 37/84* (2013.01); *C07C 39/21* (2013.01); *C12P 7/22* (2013.01)

(58) Field of Classification Search
CPC ............. C07C 37/84; C07C 39/21; C12P 7/22
See application file for complete search history.

(56) References Cited

U.S. PATENT DOCUMENTS

| 8,895,287 B2 | 11/2014 | Katz et al. |
| 9,040,269 B2 | 5/2015 | Katz et al. |
| 2012/0171186 A1* | 7/2012 | Liang ................... A61K 9/2004 424/94.1 |

FOREIGN PATENT DOCUMENTS

| CN | 101805755 | 8/2010 | |
| CN | 106242959 | * 12/2016 | ........... C07C 37/685 |
| WO | WO 2009/124967 | 10/2009 | |
| WO | WO 2011/157496 | 12/2011 | |

OTHER PUBLICATIONS

Definition of enzymolysis, https://www.dictionary.com/browse/enzymolysis, retrieved Oct. 15, 2020, 1 page.*
Sun et al., "Isolation, characterization, and antimicrobial activity of endophytic bacteria from Polygonum cuspidatum", African Journal of Microbiology Research, Vo. 7(16), Apr. 2013, pp. 1496-1504.*
Iwanowycz et al., "Emodin inhibits breast cancer growth by blocking the tumor-promoting feedforward loop between cancer cells and macrophages" Molecular Cancer Therapeutics 15(8):1931-42 (Aug. 2016).
Omar et al., "Development of an improved reverse-phase high-performance liquid chromatography method for the simultaneous analyses of trans-/cis-resveratrol, quercetin, and emodin in commercial resveratrol supplements" Journal of Agricultural and Food Chemistry 62:5812-17 (Jun. 2014).
Xiong et al., "Improving key enzyme activity in phenylpropanoid pathway with a designed biosensor" Metabolic Engineering 40:113-23 (Jan. 2017).
The International Search Report for International Application No. PCT/EP2018/052412; dated Apr. 23, 2018, pp. 1-4.

* cited by examiner

*Primary Examiner* — Rosalynd A Keys
(74) *Attorney, Agent, or Firm* — McDonnell Boehnen Hulbert & Berghoff LLP

(57) ABSTRACT

The present invention relates to a process for recovering and purifying resveratrol produced by microbial fermentation. More particularly, the present invention relates to a process for recovering and purifying resveratrol produced by yeast fermentation.

27 Claims, 7 Drawing Sheets bis-noryangonin $^1$H NMR (400 MHz, DMSO-$d_6$) δ ppm 4.40 (br s, 1 H) 5.57 (br s, 1 H) 6.55 (br d, J=15.97 Hz, 1 H) 6.76 (br d, J=8.11 Hz, 2 H) 6.99 (d, 1 H) 7.40 (br d, J=8.36 Hz, 2 H)

(bis-noryangonin)

$^{13}$C NMR (101 MHz, DMSO-$d_6$) δ ppm 86.6 (1, s 1C) 109.30 (s, 1C) 115.8 (s, 2C) 118.8 (s, 1C) 126.9 (s, 1C) 128.7 (s, 2C) 130.6 (s, 1C) 156.2 (s, 1C) 158.0 (s, 1C) 165.2 (s, 1C) 165.2 (s, 1C)

(bis-noryangonin)

RECOVERING AND PURIFYING RESVERATROL PRODUCED BY MICROBIAL FERMENTATION

CROSS-REFERENCE TO RELATED APPLICATION

This application is a U.S. national stage application under 35 U.S.C. § 371 of International Application No. PCT/EP2018/052412, filed Jan. 31, 2018, which claims priority to GB Patent Application No. 1701598.3, filed Jan. 31, 2017, all of which are explicitly incorporated by reference herein in their entirety.

The present invention relates to a process for recovering and purifying resveratrol produced by microbial fermentation. More particularly, the present invention relates to a process for recovering and purifying resveratrol produced by yeast fermentation. In another aspect, the present invention relates to a resveratrol composition. More particularly, it relates to a resveratrol composition having a reduced concentration of bisnoryangonin than has been achievable in prior art processes.

Unless otherwise indicated, reference to "resveratrol" in the present application means a reference to "trans-resveratrol".

Resveratrol, or 3,5,4'-trihydroxy-trans-stilbene, is a phytophenol belonging to the group of stilbene phytoalexins which are low-molecular-mass secondary metabolites that constitute the active defence mechanism of plants in response to infections or other stress-related events such as when the plant is under attack by pathogens such as bacteria or fungi. Stilbene compounds have been found in trees of both the angiosperm and gymnosperm type. In addition they have been found in some herbaceous plants including members of the species *Myrtaceae, Vitaceae* and *Leguminosae*. These compounds are toxic to pests such as fungi, bacteria and insects which attack these plants. Whilst stilbene compounds have been found in these plants, it should be understood that the plants which do produce stilbenes represent a small section of the plant kingdom and that very few plants are able to synthesize stilbenes or to produce them in an amount which provides them with sufficient resistance to these pests.

Whilst stilbenes are generally available in both cis- and trans-forms, the resveratrol of interest is a trans-stilbene.

Whilst resveratrol can be found in eucalyptus, spruce and lily and in food crops such as mulberries and peanuts, its most abundant natural source is in plants of the *Vitus* genus such as *Vitis vinifera, Vitis labrusca* and *Vitis muscadine* which is also known as *Vitis rotundifolia*. Thus resveratrol can be found in grapes which are used to produce wine. The resveratrol compound occurs in the vines, roots, seeds and stalks of the plant but the highest concentration can be found in the skins of the grape. It has been suggested in some studies that the grape skin may contain 50 to 100 mu.g/g of resveratrol.

Interestingly as grape skins are included in the must that is used for the production of red wine, resveratrol may be found in small quantities in red wine. However it is not present in white wine where the skins are not used in the production of the wine.

Resveratrol has been shown to have a similar antifungal activity in humans as that demonstrated in plants. In addition, it has been recognized as being useful in preventing some heart conditions and in the prevention of cancer. It is also believed to act as a phytoestrogen and to inhibit platelet aggregation. These properties have been postulated as explaining the so-called "French Paradox" where despite a low-exercise, high-fat diet, the French population has a relatively low incidence of coronary heart disease which may be due to the relatively high consumption of red wine.

More recently it has been suggested that the resveratrol may activate the SIR2 gene in yeast and the analogous human gene SIRT1 which both play a key role in extending life span. There has therefore been interest in investigating the potential use of resveratrol in extending life-span.

Although there is much interest in the use of resveratrol in addressing a variety of health issues, the difficulties associated with producing the compound restrict its availability and hence the ability to commercialise it.

Currently production processes rely on extracting resveratrol either from grape skins or from Knotweed a plant from the polygonaceae family which is grown commercially in China. Unfortunately, the extraction process is labour intensive and the yield of resveratrol is low. It is therefore desirable to provide more efficient and high yielding production processes.

A further problem with conventional extraction processes is the presence of contaminants. For example, where the resveratrol is made from knotweed, it is contaminated with emodin, which is a natural compound found in the knotweed. This is disadvantageous as emodin can induce diarrhoea if consumed. It is currently unclear at what level of concentration of emodin this side effect is noted but its presence is clearly problematic.

Further contaminants which may be present where the resveratrol is extracted from knotweed will be those derived from ground and/or air pollutants which the plants have taken up from the environment in which they are grown. For example, very high concentrations of polyaromatic hydrocarbons have been detected in commercially available resveratrol samples derived from knotweed plants grown in various locations in China. The results of analysis using gas chromatography coupled to mass spectrometry on 40 g samples of commercially available resveratrol derived from knotweed plants grown in China. These are set out in Table 1 below:

TABLE 1

| Contaminant | Sample 1 | Sample 2 | Sample 3 |
| --- | --- | --- | --- |
| Anthracene | 14 µg/kg | 15 µg/kg | 250 µg/kg |
| Benzo(a) anthracene | 0.89 µg/kg | 0.91 µg/kg | 300 µg/kg |
| Benzo(a) pyrene | 0.50 µg/kg | 0.52 µg/kg | 350 µg/kg |
| Benzo(b) fluoranthene | 0.74 µg/kg | 0.73 µg/kg | 350 µg/kg |
| Benzo(ghi) perylene | 0.52 µg/kg | <0.5 µg/kg | 260 µg/kg |
| Benzo(k) fluoranthene | <0.5 µg/kg | <0.5 µg/kg | 130 µg/kg |
| Chrysene | 1.2 µg/kg | 1.3 µg/kg | 360 µg/kg |
| Dibenzo(a,h) anthracene | <0.5 µg/kg | <0.5 µg/kg | 31 µg/kg |
| Fluoranthene | 15 µg/kg | 15 µg/kg | 940 µg/kg |
| Fluorene | 94 µg/kg | 98 µg/kg | 280 µg/kg |
| Indeno(1,2,3-cd)pyrene | <0.5 µg/kg | <0.5 µg/kg | 190 µg/kg |
| Phenanthrene | 67 µg/kg | 69 µg/kg | 860 µg/kg |
| Pyrene | 13 µg/kg | 13 µg/kg | 920 µg/kg |
| Sum PAHs (4 or less rings) | 3.3 µg/kg | 3.5 µg/kg | 1400 µg/kg |
| Sum of Heavy PAHs (5 or more rings) | 1.8 µg/kg | 1.3 µg/kg | 1300 µg/kg |
| Sum of all positive identified PAHs | 210 µg/kg | 210 µg/kg | 5200 µg/kg |

It will be understood that PAHs are polycyclic aromatic hydrocarbons which are also known as polynuclear aromatic hydrocarbons. These are chemicals that are released from incomplete combustion of organic matter, typically by the burning of fossil fuels in smelting, manufacturing, power stations, vehicles and home fires as well as by the burning of by-products of agriculture such as crop residues and dung. PAHs generally have a low solubility in water, and are predominantly seen in solid form as particulate air, soil or sediment pollution and therefore can be taken up by the knotweed. This is problematic since exposure to PAHs can be a cause of cancer in humans. In addition, they have been linked to cardiovascular disease and to poor foetal development.

In an attempt to avoid the presence of contaminants such as emodin and/or other contaminants such as PAHs, processes have been sought which use fermentation processes to produce the resveratrol rather than it being plant-derived. In this connection microbial, and in particular yeast, fermentation processes have been proposed. Examples of processes which produce resveratrol by this approach are detailed in U.S. Pat. Nos. 8,895,287, 9,040,269, WO2009/124967 which are incorporated herein by reference. These processes produce resveratrol which is free of emodin and other contaminants present when the resveratrol is extracted from knotweed such as PAHs. The results of analysis using gas chromatography coupled to mass spectrometry on 40 g samples of resveratrol produced by fermentation processes are set out in Table 2 below:

TABLE 2

| Contaminant | Sample 4 | Sample 5 |
|---|---|---|
| Anthracene | <0.5 µg/kg | 0.66 µg/kg |
| Benzo(a) anthracene | <0.5 µg/kg | <0.5 µg/kg |
| Benzo(a) pyrene | <0.5 µg/kg | <0.5 µg/kg |
| Benzo(b) fluoranthene | <0.5 µg/kg | <0.5 µg/kg |
| Benzo(ghi) perylene | <0.5 µg/kg | <0.5 µg/kg |
| Benzo(k) fluoranthene | <0.5 µg/kg | <0.5 µg/kg |
| Chrysene | <0.5 µg/kg | <0.5 µg/kg |
| Dibenzo(a,h) anthracene | <0.5 µg/kg | <0.5 µg/kg |
| Fluoranthene | <0.5 µg/kg | <0.5 µg/kg |
| Fluorene | <0.5 µg/kg | 1.3 µg/kg |
| Indeno(1,2,3-cd)pyrene | <0.5 µg/kg | <0.5 µg/kg |
| Phenanthrene | 1.5 µg/kg | 2.8 µg/kg |
| Pyrene | <0.5 µg/kg | <0.5 µg/kg |
| Sum PAHs (4 or less rings) | <0.5 µg/kg | <0.5 µg/kg |
| Sum of Heavy PAHs (5 or more rings) | <0.5 µg/kg | <0.5 µg/kg |
| Sum of all positive identified PAHs | 1.5 µg/kg | 4.8 µg/kg |

Whilst it will be understood that the product produced by fermentation processes offers advantages in that it is free of emodin and has a significantly reduced presence of PAHs, other impurities may be present. One such impurity is dihydroresveratrol. This may be present in the final product at approximately 0.01 to about 0.5 wt % which is equivalent to about 100 to about 5000 mg/kg, optionally approximately 0.01 to about 0.1 wt % which is equivalent to about 100 to about 1000 mg/kg.

A further impurity is pinosylvin. This may be present in the final product at approximately 0.05 to about 0.5 wt % which is equivalent to about 500 to about 5000 mg/kg, optionally approximately 0.05 to about 0.3 wt % which is equivalent to about 500 to about 3000 mg/kg.

Whichever process is used for the microbial production of resveratrol, it has now been found that microbially-produced resveratrol samples have a significant concentration of bisnoryangonin or derivatives thereof. Reference can be made to FIG. 1 which is an NMR plot which confirms the presence of the bisnoryangonin as an impurity in the resveratrol. All NMR experiments were performed in DMSO-ds at 25° C. using a Bruker Avance III 400 MHz spectrometer equipped with a 5 mm cryogenic BBO probe.

The bisnoryangonin is normally present in amounts of about 0.01 to about 0.02 g per g resveratrol which is equivalent to about 0.2 to 0.4 g/l titre. Whilst the presence of this level of bisnoryangonin concentration may be acceptable for some end uses of the resveratrol, it will generally be desirable to reduce its concentration particularly where the resveratrol is to be used in, for example, health supplements or in the food and beverage industry. It is therefore desirable to reduce the concentration of bisnoryangonin and derivatives thereof present in the resveratrol.

Unless otherwise indicated, reference in the present application to "bisnoryangonin" or "bisnoryangonins" as an impurity means one or more of compounds selected from the group consisting of bisnoryangonin and derivatives thereof.

Unfortunately, the processes currently used for the purification of resveratrol have not been able to satisfactorily separate out the bisnoryangonin as it co-purifies with the resveratrol. One process described to recover stilbenoids including resveratrol produced by cultivating a microorganism is described in WO2009/124967. In the process described therein, the stilbenoid produced is solid and can be separated from the culture medium by filtration, by centrifugation, by settling, decanting, or other mechanical separation methods such as flocculating and removing the microorganism such as yeast used in the production. However, it is silent as to the treatment of the recovered stilbenoid to remove impurities such as bisnoryangonin.

It is therefore desirable to provide a process which enables the recovery and purification of resveratrol that has been produced by fermentation and enables impurities such as bisnoryangonin to be removed therefrom.

The presence of bisnoryangonin and other impurities may cause the resveratrol to appear yellow or brown in colour. It will be understood that this will include any colour which could be regarded as yellow or brown including colours such as beige. Whilst the presence of colour inducing impurities may not be problematic in some uses to which the resveratrol is to be put, where it is for food or beverage use, the presence of colour inducing impurities is disadvantageous and it is therefore desirable that the recovery and purification process removes colour inducing impurities.

Thus according to the first aspect of the present invention there is provided a process for recovering and purifying resveratrol from a microbial fermentation broth said process comprising:
  (a) increasing the pH of the fermentation broth to about 10 to about 12;
  (b) separating and removing the host microbes such that a substantially microbe free liquid remains;
  (c) decreasing the pH of the substantially microbe free liquid such that crude resveratrol is precipitated;
  (d) separating the precipitated crude resveratrol;
  (e) dissolving the crude resveratrol recovered in step (c) in a purification solvent to form a crude resveratrol containing solution;
  (f) optionally contacting the solution produced in step (e) with $Al_2O_3$ and/or ion exchange resins;
  (g) contacting the solution produced in step (e) or step (f) with carbon and
  (h) crystallizing the purified resveratrol from the purification solvent, said purified resveratrol having a lower concentration of impurities including bisnoryangonin than the precipitated crude resveratrol of step (c).

By this process, it is possible to obtain resveratrol having a higher purity than has been achievable heretofore. In particular, it is possible to provide resveratrol in which the concentration of bisnoryangonin is reduced. Preferably a reduced concentration of other impurities, including colour inducing impurities, is achieved. Generally, the colour inducing impurities will be removed such that the product has a yellowness index of about 40 or less, about 30 or less, about 25 or less, about 15 or less, or about 5 or less. Additionally or alternatively, the colour inducing impurities will be removed such that the product has a whiteness index of about −50 or more, about −40 or more, about −30 or more, about −20 or more, about −10 or more, about 0 or more, about 10 or more, about 30 or more, or about 100 or more. These indices are measured in accordance with ASTM E313.

Resveratrol has limited solubility at a pH lower than about 10 and at a pH above about 12 decomposition of the resveratrol may occur and thus the pH to which the fermentation broth is adjusted in step (a) is from about 10 to about 12. In one arrangement, a pH of from about 10.5 to about 11.5 may be used. Some advantages may be noted at a pH of about 11. Any suitable means for increasing the pH of the fermentation broth in step (a) may be used. Generally this will be achieved by the addition of an alkali to the fermentation broth. Suitable alkali compositions which may be added include sodium hydroxide, potassium hydroxide, sodium carbonate, and calcium hydroxide.

The host microbes can then be removed. This removal may be carried out by any suitable means. Generally this will be achieved by filtration. Suitable means include ultrafiltration, pressure filtration, vacuum drum filtration, and cross-flow filtration. Where pressure filtration is used, this may be carried out using any suitable apparatus such as a candle filter or a filter press.

Where ultrafiltration is used to separate the host microbes, the molecular weight cut-off in the ultrafilter may be about 100 kDa or less, about 50 kDa or less, about 25 kDa or less, about 10 kDa or less or about 5 kDa or less. The flux rates and/or yields used through these various membranes may be similar. However, smaller molecular weight cut-offs may be preferred as they eliminate more impurities, which leads to increased purity of process intermediates thereby offering the potential for simpler and/or more efficient purification processes which will offer advantages in process economics. However, finer ultrafilters will require cleaning more frequently requiring process shutdown so again there is a balance to be made in the selection of the optimum molecular weight cut-off to achieve an acceptable purity without compromising the process economics by frequent shut downs for cleaning.

It will be understood that more than one separation step may be used to separate the host microbes in step (b). For example, a bulk filtration step may be followed by a concentration step, a non-limiting example of which is ultrafiltration.

Whichever means is used to carry out the separation of the host microbes, the process may include a step in which the remaining broth is concentrated before the pH is reduced in step (c). Whether a concentration step is required, may depend on the ability of the equipment used in subsequent steps to handle large volumes or the need to transport material between steps.

This optional concentration step may be achieved by any suitable means. For example evaporation, nanofiltration or reverse osmosis may be used. Particular advantages may be noted where reverse osmosis is used. Where reverse osmosis is used, it will be carried out at any suitable pressure. High pressures such as about 50 bar may be used.

The broth from which the microbes have been removed, optionally having been subjected to a concentration step, is treated such that the pH is reduced such that the resveratrol will precipitate. The pH selected will generally be above the pKa of any organic acids which may be present and so generally the pH will be selected to be from about 4.5 to about 8.5. A pH of from about 5 to about 8, from about 5.5 to about 7.5, from about 6 to about 7 or at about 6.5 may be used.

The reduction in pH can be achieved by any suitable means and is generally achieved by the addition of an acid. Any suitable acid may be used. Suitable acids include sulphuric acid, hydrochloric acid, citric acid and acetic acid, although sulphuric acid or hydrochloric acid may offer some advantages. Sulphuric acid may be preferred as it is less corrosive and so where, for example, stainless steel tanks are used, it will not cause excessive wear. Whilst hydrochloric acid is likely to be more damaging to stainless steel tanks it may offer advantages in terms of downstream processing of waste.

The precipitated crude resveratrol will then be separated from the precipitation liquor. This separation can be achieved by any suitable means but will generally be achieved by filtration.

The separated solids will then be dissolved into the purification solvent. Any suitable solvent may be used. Suitable solvents include lower alkanols such as methanol, ethanol or propanol although higher alkanols can be used. Other suitable solvents include acetone, ethyl acetate and tetrahydrofuran. Generally ethanol will be used. Dependant on the end product, ethanol may be required to be used as it is generally acceptable for regulatory approval. Where ethanol is used, it may be about 65 to about 80 vol % ethanol. In one arrangement, about 70 vol % ethanol may be used.

The dissolution may be to any suitable resveratrol concentration. Some advantages may be noted where the resveratrol concentration is in the region of from about 30 to about 50 g/l or from about 35 to about 45, or about 40 g/l.

The solution of resveratrol is then contacted with one or more absorbents, non-limiting examples of which include carbon, Aluminium Oxide, or ion exchange resins. Carbon used as an absorbent is preferably activated carbon. The carbon will absorb impurities particularly the bisnoryangonin and colour inducing impurities. This will have the benefit of producing a resveratrol product which is whiter than is generally achievable with prior art processes. This is particularly useful where the resveratrol is for food or beverage use.

Any suitable amount of carbon may be used. The resveratrol may be contacted with the carbon by any suitable means. In one arrangement, the carbon may be added to the resveratrol solution and the resultant slurry stirred. In an alternative arrangement, the resveratrol may be contacted with a bed, or a plurality of beds, of carbon. Whichever method is used, any suitable amount of carbon may be used. In one arrangement, the amount of carbon present may be from about 1.5 kg to about 2 kg per kg of resveratrol to be treated. In one alternative arrangement, the solution of resveratrol may be contacted multiple times with carbon. Thus it may be slurried repeatedly with carbon or it may be passed through a plurality of beds of carbon, or be passed a multiple number of times through a single bed. For example, the solution of resveratrol may be contacted with carbon three times either as repeated slurrying or by being passed through three beds of carbon. In this arrangement, about 0.5 kg of carbon per kg of resveratrol to be treated may be used for each contact. Other arrangements such as the use of 2 or 4 contacts with carbon may be used.

In one alternative arrangement, the solution of resveratrol may additionally be contacted with one or more other absorbents, in addition to carbon, to remove other impurities. Suitable absorbents include ion exchange resins and/or $Al_2O_3$. The other absorbent(s), where used, may be mixed with the carbon, may be present in separate layers within the same vessel or the solution of resveratrol may be passed through a bed of the other absorbent(s) before or after being contacted with the carbon.

The purified resveratrol can then be separated from the purification solvent by crystallisation. Any dihydroresveratrol or other water-soluble species, will be retained in the solvent. Any suitable endpoint concentration of the purification solvent may be used to achieve crystallisation. Where the purification solvent is ethanol, the concentration of the purification solvent may be reduced to about 40 or to about 15 vol %. The concentration may be reduced to about 30, or about 25 vol %, or about 20 vol %. In one arrangement, the reduction in ethanol concentration may be achieved by adding water to the solution, heating it and then gradually cooling the solution optionally with the addition of further water prior to filtration. For example, in one arrangement, water is added to the solution to adjust the concentration of ethanol to about 50 vol % and the solution is heated to a temperature of about 55° C. The solution may then be cooled to about 5° C. to about 10° C. over a period of several hours. Further water can then be added to reduce the ethanol concentration to about 25 vol % before the precipitated resveratrol can be removed by filtration.

Whilst a higher solvent concentration at crystallisation endpoint will result in increased purity it will lead to a decreased yield and therefore the concentration chosen for the crystallisation will be a balance between the requirements for purity and high yield.

In one alternative arrangement, the crystallisation may be achieved by evaporation of the purification solvent until the desired concentration is achieved. This evaporation may be carried out under vacuum.

In one alternative arrangement, the precipitated crude resveratrol obtained in step (d) may be subjected to a pre-crystallisation step to remove impurities, particularly water-soluble impurities, before the solution is passed to step (e) and dissolved in the purification solvent.

Where a pre-crystallisation step is present, the precipitated crude resveratrol obtained in step (d) is dissolved into a first solvent. Any suitable solvent may be used. The solvent used may be the same or different to that used as the purification solvent. Suitable solvents include lower alkanols such as methanol, ethanol or propanol although higher alkanols can be used. Other suitable solvents include acetone, ethyl acetate and tetrahydrofuran. Generally ethanol will be used. Where ethanol is used, it may be about 65 to about 80 vol % ethanol. In one arrangement about 70 vol % ethanol may be used. The first solvent will generally be at an elevated temperature to assist the dissolution. The use of an elevated temperature will also limit the volume of solvent required which offers benefits in downstream process steps. Where ethanol is used as a solvent it will typically be at a temperature of about 50° C. to about 80° C. or about 60° C. to about 70° C. In some arrangements advantages may be noted when a temperature of about 55° C. is used.

The resveratrol is then crystallised out of the first solvent solution. This may be achieved by, for example, adding water to decrease the concentration of the first solvent solution and optionally decreasing the temperature. Where the solvent used is ethanol, the concentration can be reduced to about 40 to about 15 vol %. The concentration may be reduced to about 30 vol %, or about 25 vol %, or about 20 vol %. The temperature may be decreased to about 15° C., about 10° C., about 5° C. or about 0° C. or at any lower temperature which is above the freezing point of the ethanol solution.

In one arrangement, the crude resveratrol may be dissolved in about 70 vol % ethanol at about 40 g/L and heated to about 55° C. Undissolved solids can then be removed such as by filtration. Water can then be added to adjust the ethanol concentration to about 35 vol %. The solution can then be cooled to about 5° C. to 10° C. This cooling may be carried out stepwise over a period of several hours. For example, it may be reduced to 40° C. over 1 hour, then to about 20° C. for about 1 hour and then to about 10° C. over a further hour. Further water can then be added to achieve a concentration of about 25 vol % ethanol. The filtration of the crystals can then be carried out.

Whilst a higher solvent concentration at crystallisation endpoint will result in increased purity it will lead to a decreased yield and therefore the concentration chosen for the crystallisation will be a balance between the requirements for purity and high yield.

In one alternative arrangement, the crystallisation may be achieved by evaporation of the solvent until the desired concentration of solvent is achieved. This evaporation may be carried out under vacuum.

However the crystallisation is achieved, some, preferably the majority, and most preferably all, dihydroresveratrol and some water-soluble impurities, such as phloretic acid, coumaric acid and cinnamic acid, that were present in the crude resveratrol are retained in the liquor and thereby removed from the resveratrol when the crystals are separated therefrom.

The crystals of resveratrol will be separated from the filtrate by any suitable means but generally they will be removed by filtration. Once separated, the crystals will generally be washed. This may be with water or weak ethanol such as about 25 vol % ethanol.

These pre-crystallisation steps may be repeated. If they are repeated, they will generally only be repeated once however, further repetitions may be required and can be employed where necessary. Any repetition may use the same or different conditions to those used in the first pass through these steps.

Once recovered the purified resveratrol may be dried, and/or milled, before being passed to end use processing. This may be directly passed to end use processing or it may be packaged and stored for subsequent usage.

The resveratrol recovered and purified in accordance with the present invention has a reduced content of impurities and, in particularly dihydroresveratrol and bisnoryangonin than has been achievable heretofore.

According to a second aspect of the present invention there is provided a composition comprising resveratrol which has been recovered and purified from a microbial fermentation broth in accordance with the above first aspect of the present invention.

According to a third aspect of the present invention there is provided a composition comprising at least about 70 wt % resveratrol, about 10 to about 5000 mg/kg dihydroresveratrol, and about 10 to about 5000 mg/kg pinosylvin, wherein the composition further comprises bisnoryangonin at a maximum concentration of about 5000 mg/kg as measured by dry weight ratio to resveratrol and wherein the composition is free of emodin.

The amount of resveratrol present in the composition may be at least 80 wt %. In another arrangement, it may be about 90 wt % or more. Compositions having about 95 wt % or more, about 98 wt % or more or even 99 wt % may be achieved.

The composition may additionally include water. The concentration of water present may be about 2 wt % or less.

The amount of dihydroresveratrol present in the composition may be from about 100 to about 5000 mg/kg, about 500 to about 1500 mg/kg, or about 1000 mg/kg.

The amount of pinosylvin present in the composition may be from about 500 to about 5000 mg/kg, from about 500 to about 3000 mg/kg, from about 500 to about 2500 mg/kg or from about 1000 to about 2000 mg/kg or about 1500 mg/kg.

Where present the amount of bisnoryangonin present may be from about 100 to about 1000 mg/kg or from about 200 to about 800 mg/kg or about 300 to about 500 mg/kg.

The compound may have a yellowness index of about 40 or less, about 30 or less, about 25 or less, about 15 or less, or about 5 or less. Additionally or alternatively, the compound may have a whiteness index of about −50 or less, about −40 or less, about −30 or less, about −20 or less, about −10 or less, about 0 or less, about 10 or less, about 30 or less or about 100 or less.

The composition may be dissolved or suspended in a solvent. Any suitable solvent may be used. Suitable solvents include lower alkanols such as methanol, ethanol or propanol although higher alkanols can be used. Other suitable solvents include acetone, ethyl acetate and tetrahydrofuran. Generally ethanol will be used. Dependant on the end product, ethanol may be required to be used as it is generally acceptable for regulatory approval.

The resveratrol recovered and purified in accordance with the above first aspect of the present invention or the composition of the above second or third aspect of the present invention may be used in any suitable use.

Thus according to a fourth aspect of the present invention there is provided the use of resveratrol recovered and purified in accordance with the above first aspect of the present invention or the composition of the above second or third aspect of the present invention in the manufacture of a food, beverage, health supplement, nutraceutical, polymer, heat-resistant polymer or pterostilbene.

According to a fifth aspect of the present invention there is provided the use of resveratrol recovered and purified in accordance with the above first aspect of the present invention or the composition of the above second or third aspect of the present invention in the prevention or treatment of heart conditions, prevention or treatment of cancer, inhibition of platelet formation or in extending life span.

The present invention will now be described, by way of example, with reference to the following examples and figures in which.

EXAMPLE 1

Figure 1:
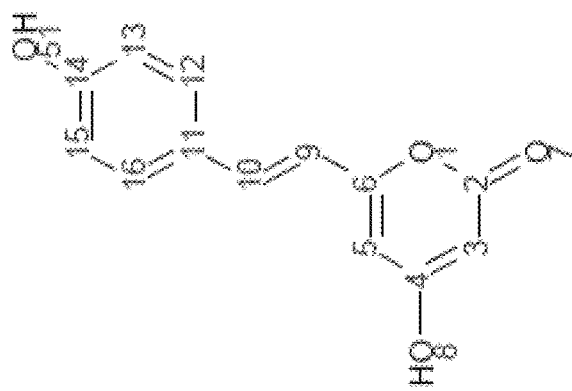
FIG. 1 is NMR data confirming that bisnoryangonin is an impurity in resveratrol.
Figure 1:
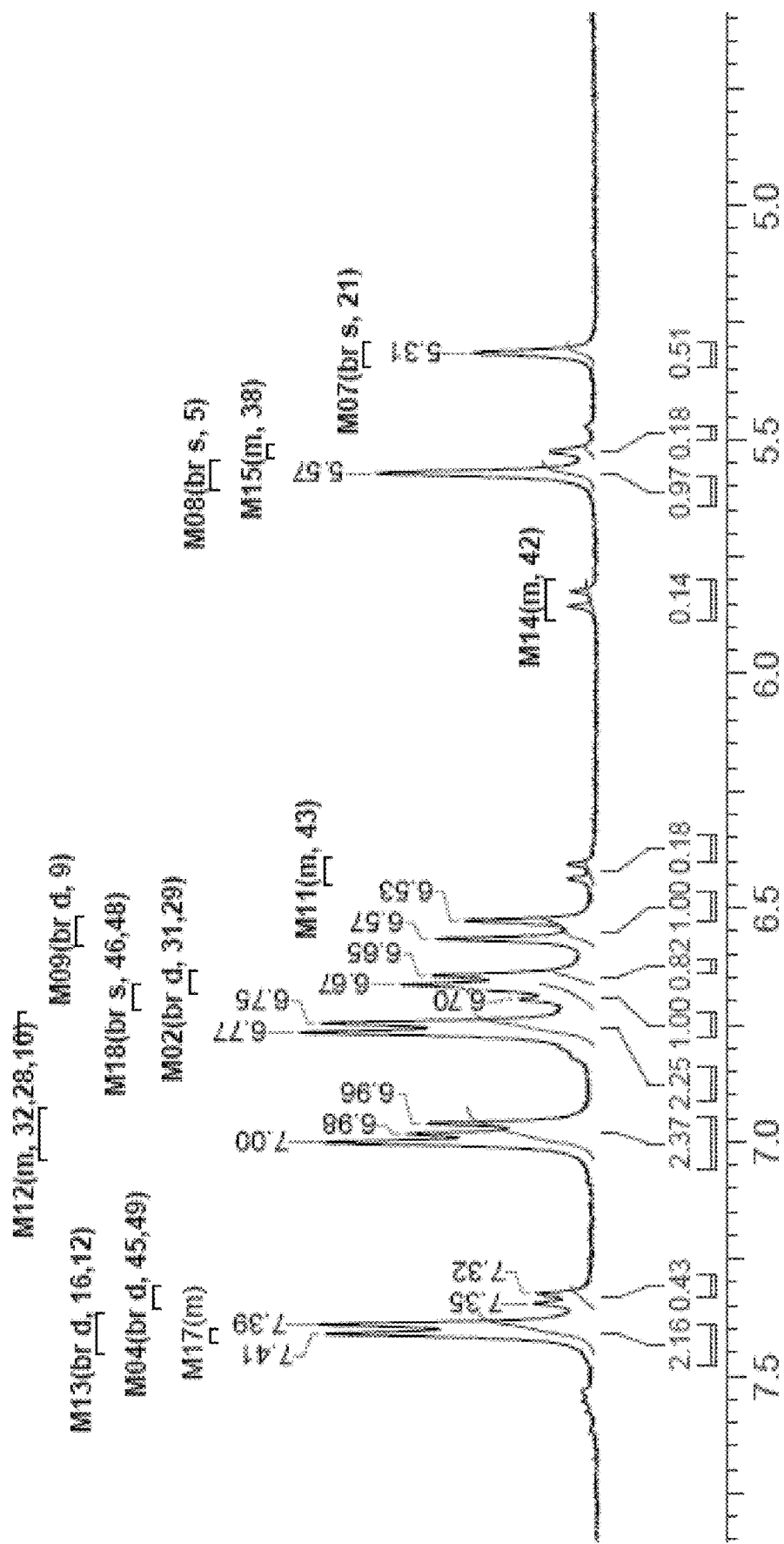
Figure 1:
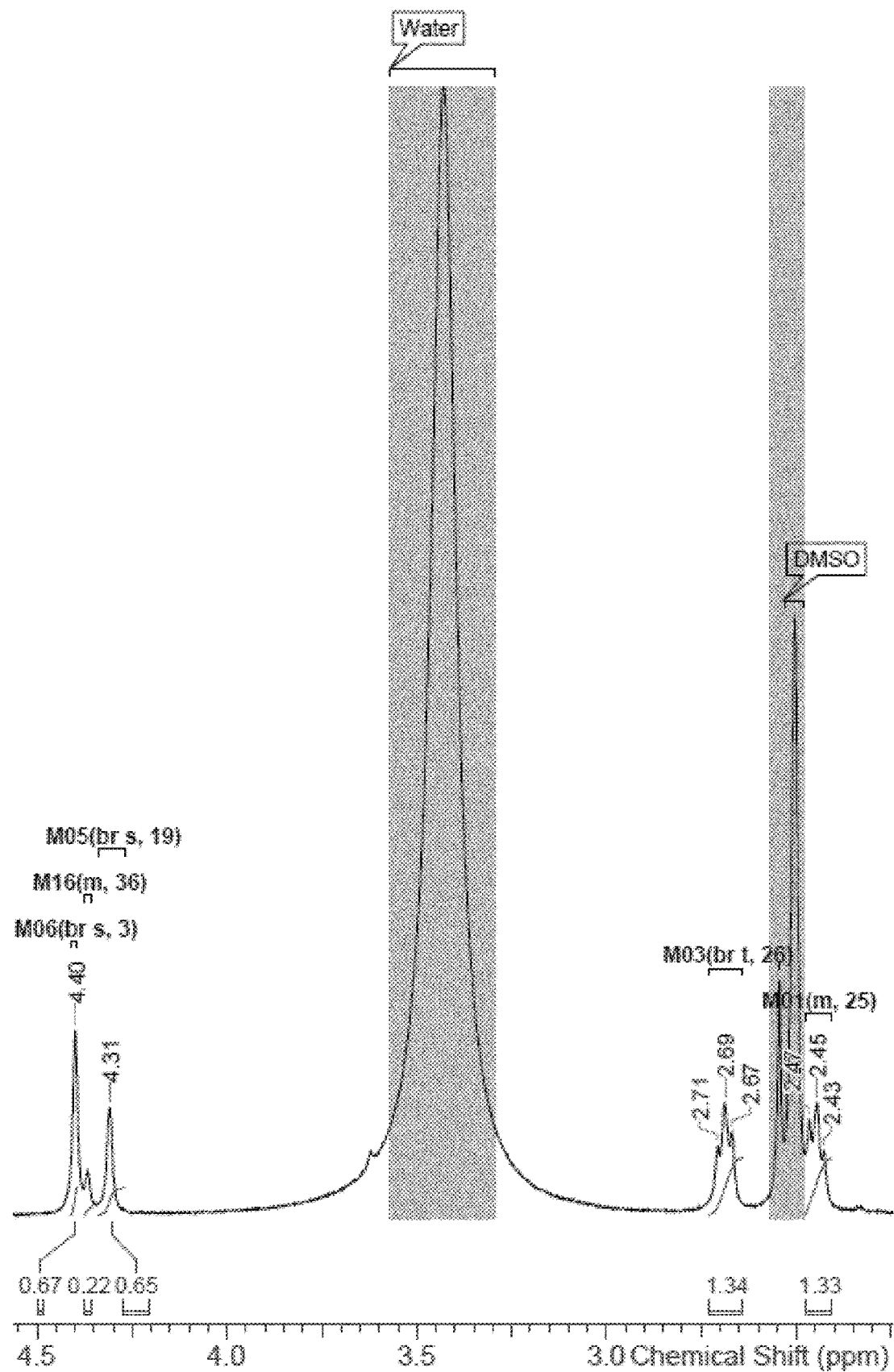

Full Downstream Process Tested at 1 L Broth Scale. Yeast Removed by Micron-Range Pressure Filter 1000 mL of broth was taken from the product of a fermentation using resveratrol-producing yeast strain EFSC4687 available from Evolve SA. The sample contained 21.6 g of trans-resveratrol. The pH of the sample was adjusted to 11 by addition of 63 mL of 30 wt % NaOH, dissolving the solid resveratrol into the liquid phase while leaving the yeast in the solid phase. The resulting yeast suspension was mixed for 1 h, and then centrifuged with a batch centrifuge for 20 min at 4400 rev/min, to deposit the yeast. 890 mL of liquid were decanted off of the yeast. 400 mL of deionized water were added and the yeast was resuspended. The suspension was then separated with the same batch centrifuge technique, and the liquid was decanted and added to the liquid that was initially decanted from the yeast. The total liquid volume recovered was 1285 mL.

The pH of the liquid was then adjusted to 7.0 over 1 hour, by the addition of 37% HCl, causing the resveratrol to precipitate as a crude solid. The resulting suspension was filtered on a laboratory pressure filter with a filter paper rated for retention of particles>0.2 micron. The crude resveratrol solids were washed with 200 mL of deionized water. The resulting wet crude resveratrol solids had a mass of 87.8 g. Moisture content was measured as 50.8 wt % using a laboratory moisture analyzer. A sample of the solids was dissolved in ethanolic solution for analysis by HPLC, and was found to contain 45 g resveratrol per 100 g dry matter. So the estimated yield of resveratrol was 19.5 g, or 90.3% of the resveratrol contained in the broth at end of fermentation.

The 87.8 g of crude wet resveratrol solids were mixed with 1080 mL of 70 vol % ethanol and heated to 55° C. for 3 hours, dissolving the solid resveratrol into ethanolic solution. The crude solids did not dissolve entirely into ethanol solution, and the remaining solids were filtered out with a vacuum filter, using a filter paper rated with a 12-25 micron exclusion size. The residual solids were washed with 220 mL of 70 vol % ethanol. This produced 1260 mL of ethanolic filtrate containing dissolved resveratrol. 2270 mL of deionized water were added to this filtrate during 2 to 4 hours, which decreased the ethanol content of the liquor to ~25 vol % and caused crystallization of the resveratrol contained in the liquor. The material was stirred overnight and cooled to 5° C. to 10° C. for 3 hours to increase the crystallization yield. The resulting crude resveratrol solids were filtered out of the crystallization liquor using a vacuum filter with 12-25 micron filter paper. The solids were washed with 200 mL of deionized water, yielding 67.9 g of wet semi-crude solids. A sample of the semi-crude material was analyzed and it was found to contain 69.5 wt % $H_2O$, with 71.8 g trans-resveratrol per 100 g of dry matter. So the estimated yield of trans-resveratrol was 14.9 g, or 76.1% of the resveratrol in the crude solids generated by acid precipitation.

The 67.9 g of wet semi-crude solids were dissolved in 517 mL of 70 vol % ethanol and mixed for 2 hours at ambient temperature (approx. 20° C.). 6.2 g of activated carbon (CECA Acticarbone ENO-PC) were added and the mixture was stirred for 2 hours, to allow for adsorption of impurities including color bodies. The carbon was then removed by vacuum filtration and washed with 75 mL of 70 vol % ethanol. A second dose of 6.2 g of activated carbon was added to the resulting filtrate, and stirred for 2 hours, to adsorb more impurities and color inducing impurities. The carbon was again removed by filtration, this time with the aid of a Celite 512 filter aid precoat. Again the carbon was washed with 75 mL of 70 vol % ethanol, yielding a total of 516 mL of ethanolic filtrate. 930 mL of deionized water were added slowly over 2 to 4 hours, which decreased the ethanol content of the liquor to about 25 vol % and caused crystallization of the resveratrol contained in the liquor. The material was stirred overnight and cooled to 5° C. to 10° C. for 3 hours to increase the crystallization yield. The resulting resveratrol solids were filtered out of the crystallization liquor using a vacuum filter with 12 to 25 micron filter paper. The solids were washed with 200 mL of deionized water, then dried overnight in a vacuum oven. This yielded 12.2 g of dried product resveratrol, or 82.2% of the resveratrol contained in the semi-crude material. The product was analyzed and found to contain 99.7 g of resveratrol per 100 g of dried product. So the overall downstream process yield was calculated as 56% (12.2 g/21.6 g). The product contained 0.04% pinosylvin and 0.02% of cis-resveratrol. The product color was analyzed according to ASTM method E308, and the yellowness and whiteness indices were calculated according to ASTM E313. The Yellowness Index was 15 and the Whiteness Index was 41.

Figure 2:
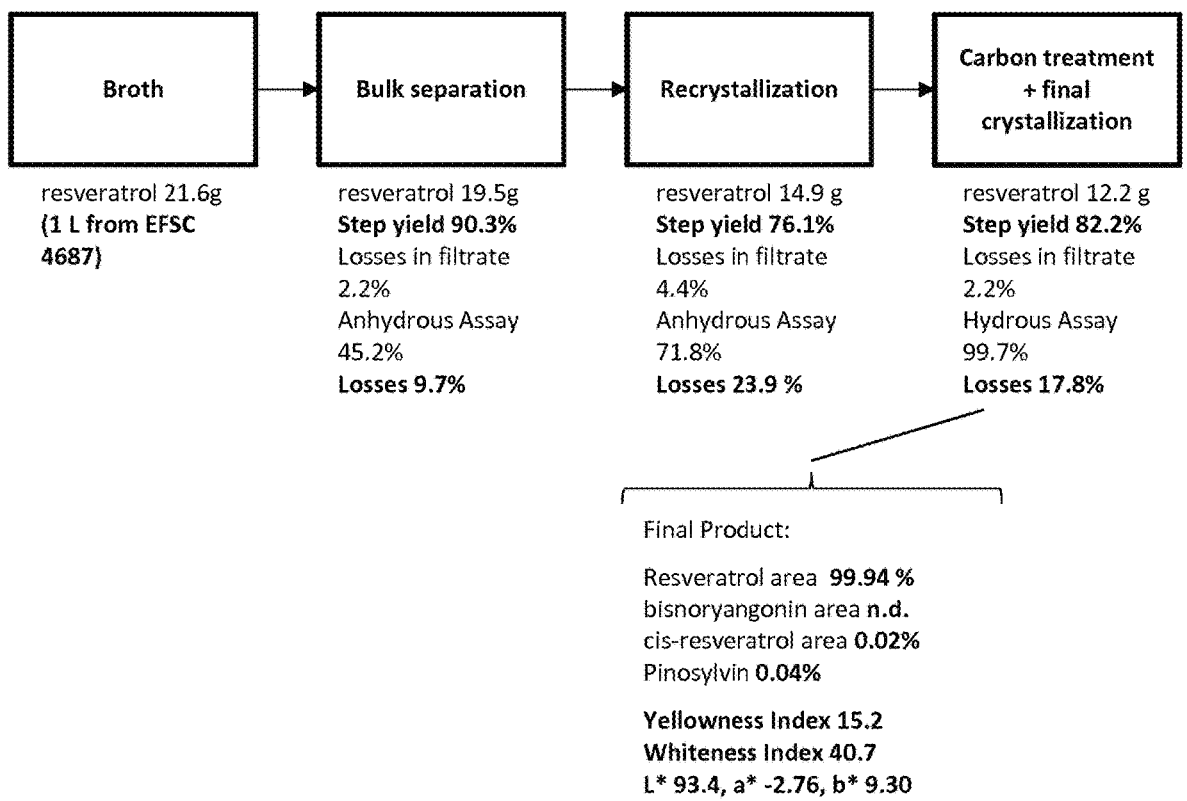
FIG. 2 is a summary of key yield and purity data for the results of Example 1.

The test parameters and results are summarized in Table 3 below and FIG. 2.

TABLE 3

| Op # | Operation | Lab parameters | Lab example |
|---|---|---|---|
| 1 | Add base to dissolve resveratrol | Adjust pH to 11.0<br>Add ~0.06 L of 30 wt % NaOH per L of broth<br>Mix 1 h | 1000 mL broth (21.6 g trans-resveratrol)<br>63 mL of 30% NaOH<br>Mix 1 h |
| 2 | Separate yeast solids from liquid product | Batch centrifuge, 4400 rpm × 20 min.<br>Separate supernatant (~0.89 L supe per L broth). Wash solids w 0.4 L wash water per L of broth, add to first supernatant. | 400 mL wash water<br>1285 mL total supernatant + wash volume |
| 3 | Neutralize pH with $H_2SO_4$ | Adjust pH to 7.0<br>~0.007 L of 96% $H_2SO_4$ per L of supernatant | 37% HCl |
| 4 | Separate crude resveratrol from suspension | Pressure filter, wash solids with 0.15 L of water per L of slurry filtered | Pressure filter 1360 mL of neutralized slurry<br>+200 mL of wash water<br>–>1580 mL filtrate + 87.8 g wet crude (50.8 wt % $H_2O$, 43.2 g dry matter, 19.5 g trans-resv) |
| 5 | Dissolve wet crude solid in ethanol | Measure dry matter content, add 25 L of 70 vol % EtOH/kg crude (dry basis), mix 3 h at 55° C. | 1080 mL of 70 vol % EtOH added to 87.8 g wet crude |
| 6 | Filter out undissolved solids | Vacuum filter, wash with 5 L of 70 vol % EtOH/kg crude (dry basis) | Vacuum filter (12-25μ filter paper)<br>Wash with 220 mL of 70 vol % EtOH |
| 7 | Slowly add water, cool and hold to crystallize | Add 53 L water per kg crude (dry basis) to adjust ethanol content to 25 vol %, dropwise for ~2-4 h (overnight). Cool to 5-10° C. for 3 h | 1260 mL filtrate<br>Add 2270 mL H2O |
| 8 | Filter out semi-crude, water wash | Vacuum filter, wash with 5 L water/kg crude | Vacuum filter (12-25μ filter paper)<br>Wash with 200 mL water<br>–>3560 mL filtrate<br>67.9 g wet semi-crude<br>(69.5% $H_2O$, 20.7 g dry matter, 14.9 g trans-resv) |
| 9 | Dissolve wet semi-crude in ethanol | Measure dry matter content, add 25 L of 70 vol % EtOH/kg crude (dry basis), mix 2 h at ambient temperature | 517 mL of 70 vol % EtOH |
| 10 | Add first dose of carbon + mix | Add 0.3 kg C/kg crude (dry basis), mix 2 h at ambient temperature | 6.2 g Acticarbone ENO-PC |
| 11 | Filter out first carbon dose, wash with ethanol | Vacuum filter, wash with 3.6 L of 70 vol % EtOH 1 kg crude (dry basis) | Filter, wash w/75 mL of 70 vol % ethanol |
| 12 | Add second dose of carbon + mix | Add 0.3 kg C/kg crude (dry basis), mix 2 h at ambient temperature | 6.2 g Acticarbone ENO-PC |

TABLE 3-continued

| Op # | Operation | Lab parameters | Lab example |
|---|---|---|---|
| 14 | Filter out second carbon dose, wash with ethanol | Vacuum filter over Celite, wash with 3.6 L of 70 vol % EtOH/kg crude (dry basis) | Precoat with 1 g Celite 512 Filter, wash w/75 mL of 70 vol % ethanol |
| 15 | Slowly add water, cool and hold to crystallize | Add 45 L water per kg crude (dry basis) to adjust ethanol content to 25 vol %, dropwise for ~2-4 h (overnight). Cool to 5-10° C. for 3 h | 516 mL filtrate Add 930 mL of water |
| 16 | Filter out product, water wash | Vacuum filter, wash with 5 L water/kg crude (dry basis) | Vacuum filter (12-25μ filter paper) Wash with 200 mL water |
| 17 | Dry | Vacuum oven overnight | Dry overnight in vacuum oven 12.2 g dried product Exceeded purity + color specifications |

EXAMPLE 2

Full Downstream Process Tested at 8 L Broth Scale. Yeast Removed by 100 kDa Ultrafilter 8 L of broth was taken from the product of a fermentation using resveratrol-producing yeast strain EVST21811 available from Evolva SA. The sample contained 166 g of trans-resveratrol. 0.5 L of 30% NaOH was added to increase the pH to 11 and the material was mixed for 1 hour. The sample was then difiltered on an Alfa Laval M20 tangential flow filtration unit, using an Alfa Laval 0.6 m² GR40PP filtration element. The GR40PP filter had a nominal molecular weight cutoff of 100 kDa. The filter was operated at 3 to 4 bar trans-membrane pressure. 46 L of permeate were collected, and the retentate was concentrated to 2 L at the end of the experiment. The permeate was then concentrated to 9 L using the same tangential flow filtration unit, with an Alfa Laval RO98pHt filtration element. The filter was operated at 25 to 30 bar trans-membrane pressure. 60 mL of 96% $H_2SO_4$ were added to neutralize the pH to 7.0 and precipitate crude resveratrol. The resulting crude resveratrol solids were filtered out of the suspension using a pressure filter, and were washed with 1.4 L of deionized water. This yielded 520 g of wet crude resveratrol. A sample of the material was analyzed and it was found to contain 63 wt % water, and 70 g resveratrol per 100 g of dry matter. So a bulk separation yield of 135 g resveratrol was calculated, corresponding to 86% of the resveratrol contained in the fermentation broth.

A sample of 23.2 g of the crude resveratrol was purified, following the same approach described in Example 1. However in this case, the crude material had a higher purity (70% versus 45% in Example 1) and only a single carbon treatment was necessary to purify the material to target specifications. After the ethanol crystallization, the "semi-crude" resveratrol solids contained 97.6 g of resveratrol per 100 g of dry sample, a much greater purity than that in Example 1 (which was 72%). Without being bound by any particular theory, it is believed to be likely due to the removal of proteins by the ultrafiltration; likely some proteins are soluble at pH of 11 and permeate the micron-rated filter, and then co-precipitate with resveratrol upon acid precipitation. Subsequently those proteins may impair purification process performance. The semi-crude product was analyzed and contained 5.25 g of resveratrol, 87.5% of the resveratrol fed to the crystallization process.

The "semi crude" resveratrol sample was then dissolved in ethanol and contacted with a single carbon dose of 3.0 g (CECA Acticarbone ENO-PC), and stirred for 2 hours before removing the carbon by vacuum filtration. Water was added to crystallize the product. The final product contained 5.12 g of resveratrol, 97.6% of the resveratrol contained in the semi-crude material. The purification yield was therefore 85%, and the overall downstream process yield was 73%. The product contained 98.7 g of resveratrol per 100 g of dry matter. Its colour was analysed and the Yellowness and Whiteness Indices were 15 and 37, respectively.

The test parameters and results are summarized in Table 4 below and FIG. 3.

TABLE 4

| Op# | Operation | Lab parameters | Lab example |
|---|---|---|---|
| 1 | Add base to dissolve resveratrol | Adjust pH to 11.0 Add ~0.06 L of 30 wt % NaOH per L of broth Mix 1 h | 8 L broth (166 g resveratrol) 0.5 L of 30% NaOH Mix 1 h |
| 2 | Separate yeast solids from liquid product | Alfa Laval M20, 0.6 m² of GR40PP membranes 3-4 bar TMP, 10 L/min cross-flow No pre-concentration, just diafiltration 5.8 permeate volumes/broth volume Need to add NaOH to maintain pH in retentate | 8 L broth 46 L permeate 2 L retentate |

TABLE 4-continued

| Op# | Operation | Lab parameters | Lab example |
|---|---|---|---|
| 3 | Concentrate liquid | Alfa Laval M20, 0.6 m² of RO98pHt membranes 25-30 bar TMP, 9 L/min cross-flow 5.1x volumetric concentration factor 1.1 L of concentrate per L of broth | 46 L permeate 9 L concentrate |
| 4 | Neutralize pH with $H_2SO_4$ | Adjust pH to 7.0 ~0.007 L of 96% $H_2SO_4$ per L of concentrate | 60 mL of 96% $H_2SO_4$ added slowly |
| 5 | Filter out crude | Pressure filter, wash solids with 0.15 L of water per L of slurry filtered | Pressure filter 9 L of neutralized slurry +1.4 L of wash water –>520 g wet crude (63% water, 193 g dry matter, 135 g trans-resv) |
| 6 | Dissolve wet crude solid in ethanol | Measure dry matter content, add 25 L of 70 vol % EtOH/kg crude (dry basis), mix 3 h at 55° C. | |
| 7 | Filter out undissolved solids | Vacuum filter, wash with 5 L of 70 vol % EtOH/kg crude (dry basis) | |
| 8 | Slowly add water, cool and hold to crystallize | Add 110 L water per kg crude (dry basis) to adjust ethanol content to 15 vol %, dropwise for ~2-4 h (overnight). Cool to 5-10° C. for 3 h | |
| 9 | Filter out semi-crude, water wash | Vacuum filter, wash with 5 L water/kg crude | |
| 10 | Dissolve wet semi-crude in ethanol | Measure dry matter content, add 25 L of 70 vol % EtOH/kg crude (dry basis), mix 2 h at ambient temperature | |
| 11 | Add first dose of carbon + mix | Add 0.3 kg C/kg crude (dry basis), mix 2 h at ambient temperature | |
| 12 | Filter out first carbon dose, wash with ethanol | Vacuum filter over Celite, wash with 3.6 L of 70 vol % EtOH/kg crude (dry basis) | |
| 13 | Slowly add water, cool and hold to crystallize | Add 45 L water per kg crude (dry basis) to adjust ethanol content to 25 vol %, dropwise for ~2-4 h (overnight). Cool to 5-10° C. for 3 h | |
| 14 | Filter out product, water wash | Vacuum filter, wash with 5 L water/kg crude | |
| 17 | Dry | Vacuum oven overnight | |

EXAMPLE 3

Effect of pH on Performance During Bulk Separation Under Alkaline Conditions

The selection of pH for the alkaline dissolution of resveratrol is critical. If the pH is too low, resveratrol will have poor solubility. If the pH is too high, resveratrol may decompose or react with other broth components. A series of tests was performed at pH values of 10, 11, and 12 using 1 L samples of a resveratrol-containing broth. The pH of the broth samples was adjusted with NaOH, and the material was mixed for 1 hour before the yeast was filtered out using a micron-rated pressure filter. The residual solids were washed with water, and the resveratrol in the resulting filtrates were precipitated with 37% HCl. The crude resveratrol was then filtered out of the resulting suspensions and vacuum dried.

Figure 3:
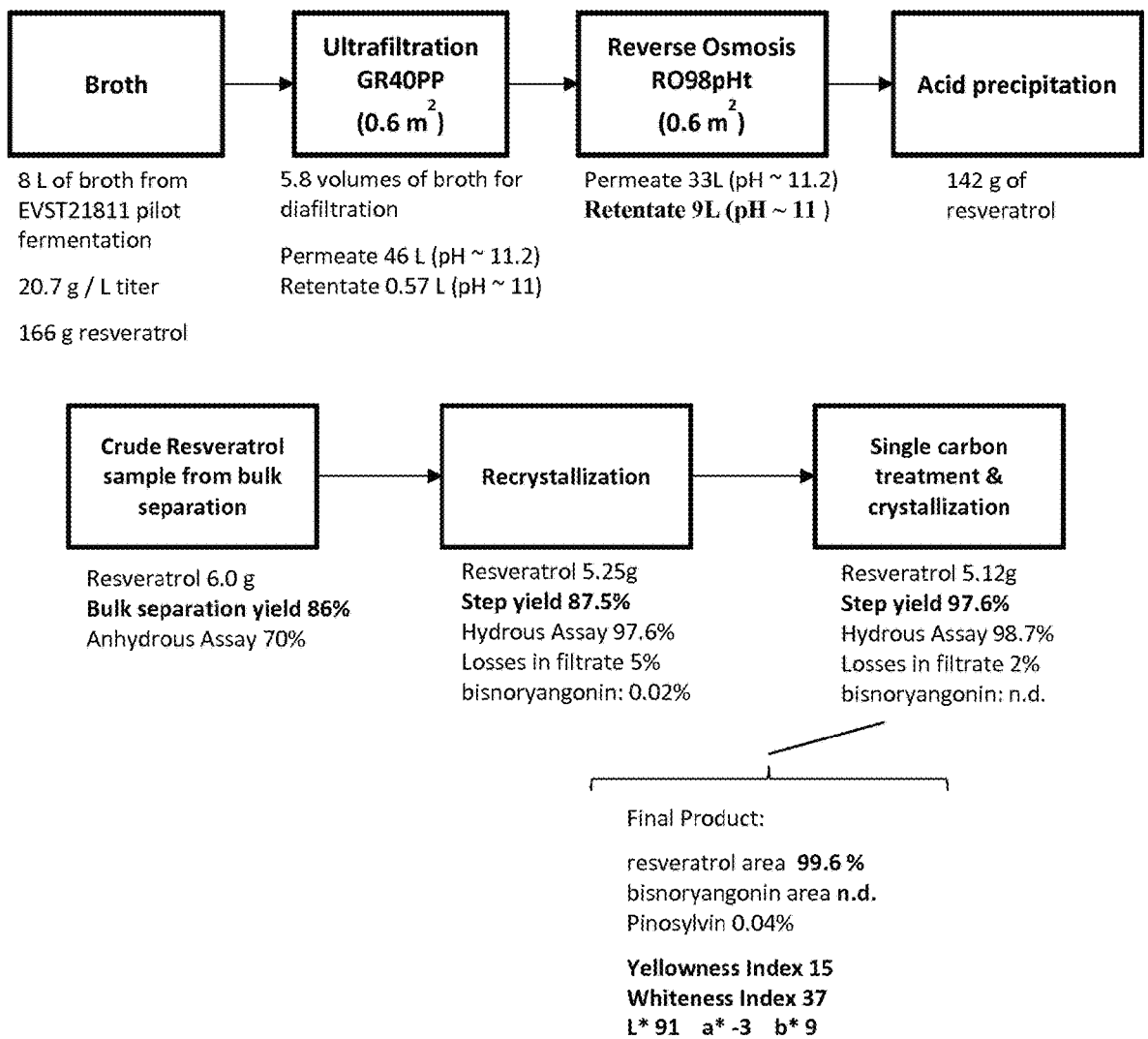
FIG. 3 is a summary of key yield and purity data for the results of Example 2.

The results of the tests are summarized in FIG. 3.

At pH 10, the yield was low (18%), and the material was brown. At pH 11 the yield was high (94%), and the material was a light beige colour. At pH 12 the yield was intermediate (72%), and the material was brown. The resveratrol content of the resulting product increased from 56 wt % at pH 10 to 64 wt % at pH 11, and increased further to 72 wt % at pH 12.

Figure 4:
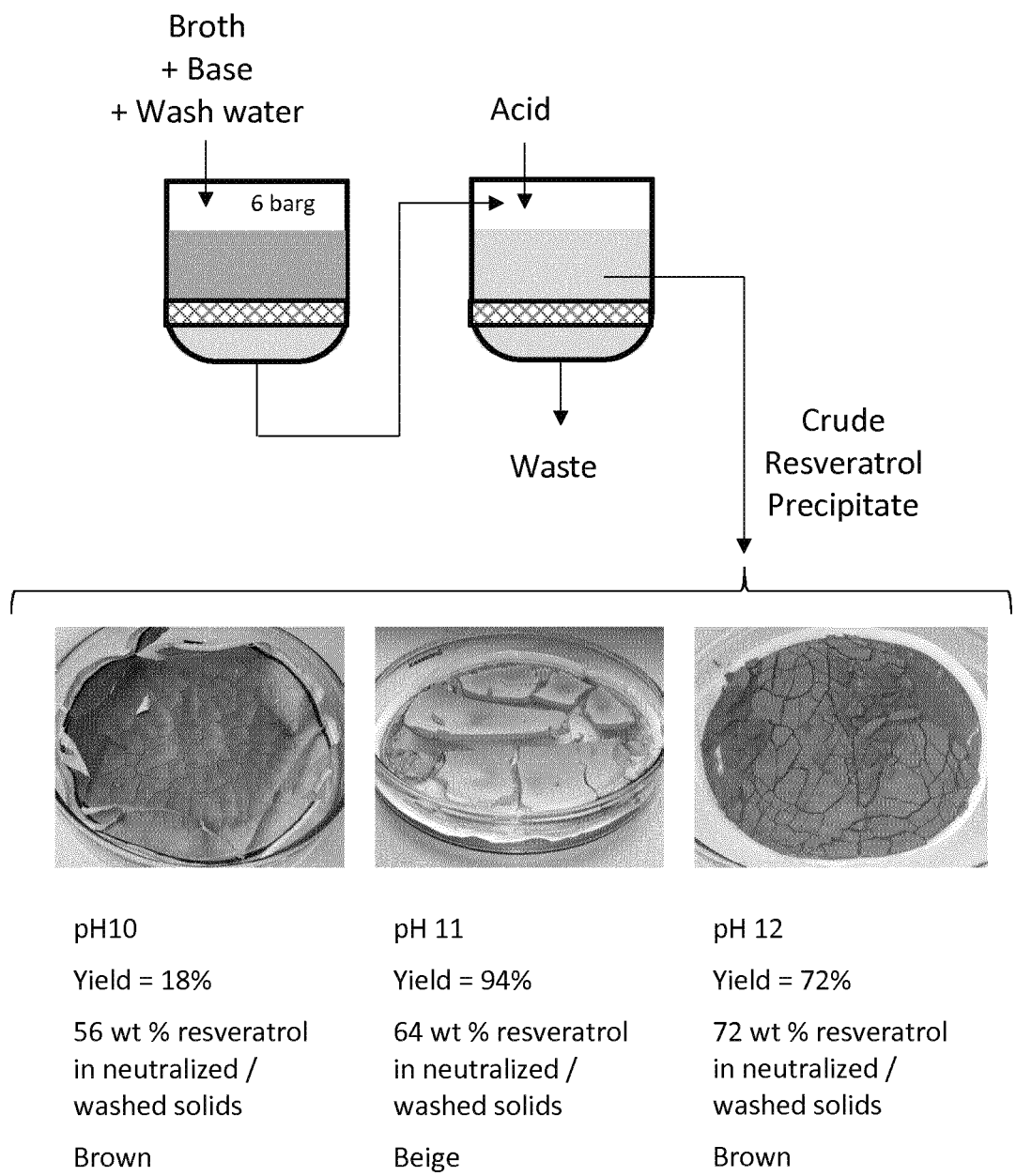
FIG. 4 is a summary of the experiments described in Example 3.
Figure 5:
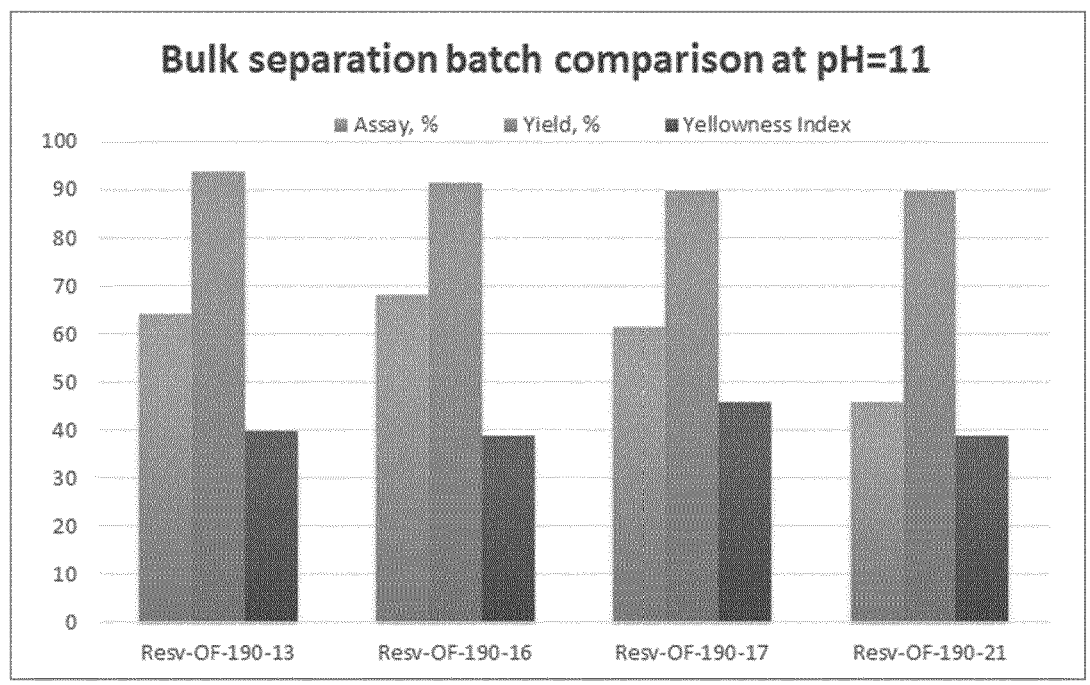
FIG. 5 is a graph illustrating the testing of bulk separation at pH11, repeated for various fermentation batches.

Based on the high yield observed at pH 11, this test was repeated several times, using broth samples from several batches. The results are summarized in FIG. 4. The process yield was very reproducible, with results from 90 to 94% shown in FIG. 4. The purity of the resulting crude resveratrol was more variable, and ranged from 46% to 68%.

EXAMPLE 4

Effect of Ultrafilter Molecular Weight Cutoff Rating on Performance During Yeast Filtration Under Alkaline Conditions When using ultrafiltration for yeast filtration at elevated pH, it has been found that the use of an ultrafilter with a lower molecular weight cutoff significantly increases the purity of the crude resveratrol after acid precipitation, without significant impairment of filtration rate. The stability of the filtrate at pH 11 is also improved with use of an ultrafilter with lower molecular weight cutoff. Both of these attributes are advantageous for processing.

A 129 L broth sample and a 96 L broth sample were processed using an Alfa Laval M38 ultrafilter at pH 11. Three ultrafiltration membranes were tested, with molecular weight cutoffs of 5, 25, and 100 kDa. The filtration performance results are summarized in Table 5 below. After adjusting pH to 11, the yeast suspensions were concentrated by a factor of 2.5-3, and then diafiltered while maintaining pH at 11 in the retentate. The filtrates were subsequently concentrated by reverse osmosis and precipitated with sulfuric acid. The resulting crude resveratrol materials were filtered out of suspension and analyzed. Yields were comparable for all three materials, approximately 78%. The purity of the materials was analyzed and the results are summarized in Table 6. The crude resveratrol produced with a 100 kDa ultrafilter contained 71.4% resveratrol. The crude resveratrol produced with the 25 kDa and 5 kDa ultrafilters was comparable in purity (79.8% and 79.2% respectively).

It is advantageous for process intermediate materials to have a high degree of stability, so that they can be processed over time without the need for immediate processing on equipment with high capacity. The various filtrates from the ultrafiltration tests were concentrated by reverse osmosis and held at pH 11 for 3 to 7 days at 5° C. to 8° C. to evaluate their stability. The results are summarized in Table 7 below. The product decomposition is a comparison between the composition at the time of production and that measured 7 days after production. The stability improved monotonically as the molecular weight cutoff of the ultrafilter was decreased from 100 kDa to 25 kDa to 5 kDa. 11%, 7%, and 5% of the resveratrol was decomposed in the respective tests.

TABLE 7

|  | Nominal Molecular Weight Cutoff | Original Concentration (g/L) | After pH Neutralization (g/L) | Product Decomposition |
|---|---|---|---|---|
| EFSC 21811 GR40PP (100 kDa) | 100 kDa | 15.9 | 14.2 | 10.7% |
| GR60PP (25 kDa) | 25 kDa | 26.7 | 24.89 | 7% |
| GR90PP (5 kDa) | 5 kDa | 24.7 | 23.4 | 5% |
| EFSC4687 GR40PP (100 kDa) | 100 kDa | 16.43 | 14.54 | 11.5% |

EXAMPLE 5

Semi Crude Crystallisation 20 g of crude resveratrol was dissolved in 500 ml of 70 vol % of ethanol. This was stirred for one hour at 55° C. and filtered through filter paper for the retention of particles having a size greater than 0.2 microns to remove any undissolved solids. These solids were washed with 60 ml 70 vol % ethanol. After filtration 560 ml of filtrate was collected. This was diluted with 560 ml of water to have a 35 vol % ethanol concentration. The temperature was maintained at 55° C. during the water addition. The diluted filtrate was then cooled to 5° C. to 10° C. over a period of 3 to 4 hours. This was done stepwise as follows: 55° C. to 40° C. for one hour, 40° C. to 20° C. for one hour and 20° C. to 5° C. for one hour. 448 ml water was added to adjust the concentration to 25 vol % and the temperature was maintained at 5° C. and stirred for one hour before the crystals were separated by filtration. The crystals were filtered through filter paper rated for retention of particles having a size greater than 0.2 microns and washed with 50 ml of deionised water.

TABLE 5

|  | EVST 21811 w/SAG790LV 2016-125 (129 L) | | | EFSC 4687 w/J647 2016-167 (96 L) |
|---|---|---|---|---|
| Membrane material | GR40PP | GR60PP | GR90PP | GR40PP |
| Nominal molecular weight cutoff | 100 kDa | 25 kDa | 5 kDa | 100 kDa |
| Surface Area | 0.75 m² | 0.75 m² | 0.75 m² | 2.25 m² |
| Cross Flow |  | ~25 L/min |  | ~25 L/min |
| Flux | 46-29 L/m²/h | 46-32 L/m²/h | 42-28 L/m²/h | 29-36 L/m²/h |
| Trans-membrane pressure |  | 3-3.2 bar |  | 3-3.2 bar |
| Retentate VCF (volumetric concentration factor) |  | 3x |  | 2.5x |
| Temperature |  | ~30° C. |  | ~30° C. |
| Permeate volumes | 44.6 L | 44.0 L | 46.4 L | 101 L |
| Diafiltration Volume |  | 52.7 L |  | 38.8 L |
| Retentate Volume |  | 44.9 L |  | 42.5 L |
| NaOH added |  | 8 L |  | 4.1 L |
| Water flux recovery after cleaning | 97% | 47% | 52% | 82% |

TABLE 6

| Membrane (MWCO) | Assay of Crude Precipitate (g trans-resveratrol per g dry matter) |
|---|---|
| GR40PP (100 kDa) | 71.4% |
| GR60PP (25 kDa) | 79.8% |
| GR90PP (5 kDa) | 79.2% |

Final Product Crystallisation 13.68 g of semi crude resveratrol was dissolved in 320 ml of 70 vol % ethanol. 6.5 g of CECA acticarbone ENO-PC was added and the resulting mixture stirred for 2 hours. The carbon was then removed by filtration using filter paper for retention of particles having a size greater than 0.2 microns. The resultant cake was washed with 20 ml of 70 vol % ethanol. 340 ml of filtrate was collected. 136 ml of water was added to form an ethanol concentration of 50 vol % ethanol. The solution was heated to 55° C. for one hour. The solution was then cooled to 5 to 10° C. over a period of 3 to 4 hours. This was done stepwise as follows: 55° C. to 40° C. for one hour, 40° C. to 20° C. for one hour and 20° C. to 5° C. for one hour. 476 ml water was added to adjust the concentration to 25 vol % and the temperature was maintained at 5° C. and stirred for one hour before the crystals were separated by filtration. The crystals were filtered through filter paper rated for retention of particles having a size greater than 0.2 microns and washed with 50 ml of deionised water.

Further details of the filtrations are set out in Table 8

TABLE 8

|  | Cooling Crystallisation | Anti-Solvent Crystallisation |
|---|---|---|
| Resveratrol Concentration | 40 g/L | 40 g/L |
| Assay | 96.35 | 95.93 |
| Related Impurities | Bisnoryangonin 0.39% a/a Dihydro 0.06% w/w Pinosylvin 0.11% w/w | Bisnoryangonin 0.31% a/a Pinosylvin 0.11% w/w |
| Yield | 77% | 75% |
| Losses in Filtrate | 3% | 2% |
| Filtration time (min) | 2.24 | 35 |
| Cake Thickness | ~3 mm | ~3 mm |
| Appearance | Crystalline | Less Crystalline |

EXAMPLE 6

9 L of microbial fermentation broth comprising resveratrol at pH 6.3 was processed using Alfa Laval M20. Four ultrafilters were tested, GR40PP (100 kDa), GR60PP (25 kDa), GR80PP (10 kDa) and GR90PP (5 kDa). The filtration performance is set out in Table 9.

TABLE 9

Filtration summary

| | GR40PP | GR60PP | GR80PP | GR90PP |
|---|---|---|---|---|
| Nominal molecular weight cutoff | 100 kDa | 25 kDa | 10 kDa | 5 kDa |
| Surface Area | 0.108 m² | 0.072 m² | 0.072 m² | 0.072 m² |
| Cross Flow | | ~9 L/min | | |
| TMP | | 4-5 bar | | |
| Flux rates VCF1 (L/m²/h) | 50 | 66 | 42 | 42 |
| VCF2 (L/m²/h) | 44 | 75 | 42 | 58 |
| Diafiltration | 72 | 75 | 108 | 117 |
| Temperature | | ~25° C. | | |
| Diafiltration | | 9 L | | |

TABLE 9-continued

Filtration summary

| | GR40PP | GR60PP | GR80PP | GR90PP |
|---|---|---|---|---|
| Volume Retentate | | 1 L | | |
| Volume Assay | 70.72% | 86.57% | 87.94% | 85.68% |

The filtration was carried out after adjusting the pH to 11 and then diafiltrated while maintaining the pH of the retentate at 11. The filtrates from each membrane was collected separately and precipitated with sulfuric acid. The yields for all four membranes were comparable at 98.61%. The purity of the material was calculated. The results are set out in for the bulk separation in Table 10 and after ultrafiltration in Table 11.

TABLE 10

| | Concentration/ Assay | Volume/ Weight | Resveratrol | Resveratrol in Crude Filtrate | Yield/ Losses |
|---|---|---|---|---|---|
| Broth | 19.92 g/L | 9 L | 179.3 g | | |

TABLE 11

| | Concentration/ Assay | Volume/ Weight | Resveratrol | Resveratrol in Crude Filtrate | Yield/ Losses |
|---|---|---|---|---|---|
| UF Retentate | 1.77 g/L | 1 L | 1.77 g | | 0.9% |
| GR40PP | 70.72% | 71.1 g | 50.28 g | 0.5 g | 98.64% |
| GR60PP | 86.57% | 79.6 g | 68.91 g | 0.2 g | |
| GR80PP | 87.94% | 31.9 g | 28.05 g | 0.02 g | 0.7% (in filtrates) |
| GR90PP | 85.68% | 34.5 g | 29.56 g | 0.6 g | |

The crude material from GR80PP (10 kDa) and GR90PP (5 kDa) was processed into decolouring without going into pre-crystallisation. The carbon treatment was effective in removing colour inducing impurities along with other impurities including bisnoryangonin. The crude material contained about 1% of bisnoryangonin and was removed with the carbon treatment. The results are set out in Table 12. The crude intermediate was dissolved in 70 vol % ethanol at 40 g/L and heated to 55° C. for one hour to dissolve everything into solution. The solution was treated with CECA ActiCarbone ENO-PC in three doses (1.5 kg of carbon for 1 kg of resveratrol). The suspension was stirred for 2 hours at 40° C. and the carbon was removed by vacuum filtration using black ribbon filter paper. The carbon cake was washed with 5× volumes to 1 g of resveratrol 70 vol % ethanol. The filtration and washing was repeated for each of the doses with carbon. The results are set out in Table 13.

TABLE 12

| | | | | |
|---|---|---|---|---|
| Bulk Separation Yield | 98.6% | 98.6% | 98.6% | 98.6% |
| Crude Assay | 87.94% | 87.94% | 85.68% | 85.68% |
| Carbon Dose | 1.5 kg/1 kg In Three Steps | 1.5 kg/1 kg In Three Steps | 1.5 kg/1 kg In Three Steps | 1.5 kg/1 kg In Three Steps |
| Carbon and Crystallization Yield | 70% | 67% | 71% | 68% |
| Final Assay | 98.45% | 98.81% | 98.35% | 99.41% |
| Colour Specification | YL24 WI 14 L*91 a*-2 b* 14 | YL 12 WI 51 L*93 a*-1 b* 7 | YL 15 WI 43 L*94 a*-3 b* 9 | YL 14 WI 43 L*93 a*-2 b* 8 |
| Impurity Profile | Coumaric acid 0.09% w/w Dihydroresveratrol 0.33% w/w Bisnoryangonin Impurity 0.05% a/a Pinosylvin 0.07% w/w | Coumaric acid 0.14% w/w Dihydroresveratrol 0.3% w/w Bisnoryangonin Impurity 0.07% a/a Pinosylvin 0.06% w/w | Coumaric acid 0.09% w/w Dihydroresveratrol 0.3% w/w Bisnoryangonin Impurity 0.07% a/a Pinosylvin 0.07% w/w | Coumaric acid 0.15% w/w Pinosylvin 0.07% w/w |
| Overall Yield | 69% | 66% | 70% | 67% |

TABLE 13

| Before Carbon Treatment (% a/a) | |
|---|---|
| Crude resveratrol GR80PP | 1.25 |
| Crude resveratrol GR90PP | 1.25 |
| After Carbon Treatment (% a/a) | |
| Final crystals GR80PP | Not detected |
| Final crystals GR90PP | Not detected |

The invention claimed is:

1. A process for recovering and purifying resveratrol from a microbial fermentation broth said process comprising:
   (a) increasing the pH of the fermentation broth to about 11;
   (b) separating and removing the host microbes such that a substantially microbe free liquid remains;
   (c) decreasing the pH of the substantially microbe free liquid to a value which is no less than about 7 to about 8.5 such that crude resveratrol is precipitated;
   (d) separating the precipitated crude resveratrol;
   (e) dissolving the crude resveratrol recovered in step (c) in a purification solvent to form a crude resveratrol containing solution;
   (f) contacting the solution produced in step (e) with one or more absorbents; and
   (g) crystallizing the purified resveratrol from the purification solvent, said purified resveratrol having a lower concentration of impurities including bisnoryangonin than the precipitated crude resveratrol of step (c).

2. The process according to claim 1 where the one or more absorbents are selected from carbon, optionally activated carbon, ion exchange resins, and/or $Al_2O_3$.

3. The process according to claim 1 where step (f) comprises the steps of:
   i) contacting the solution produced in step (e) with one or more absorbents selected from ion exchange resins and/or $Al_2O_3$; and
   ii) contacting the solution produced in step i) with carbon, optionally activated carbon.

4. The process according to claim 1, wherein the host microbes are removed by ultrafiltration, pressure filtration, vacuum drum filtration, or cross-flow filtration.

5. The process according to claim 4, wherein the host microbes are removed by ultrafiltration using an ultrafilter having a molecular weight cut-off of about 100 kDa to about 5 kDa or less.

6. The process according to claim 1, wherein the process includes a concentration step before step (c).

7. The process according to claim 6, wherein the concentration step is carried out by reverse osmosis.

8. The process according to claim 1, wherein the reduction of pH in step (c) is achieved by the addition of sulphuric acid or hydrochloric acid.

9. The process according to claim 1, wherein the purification solvent is selected from methanol, ethanol, propanol, acetone, ethyl acetate, and tetrahydrofuran.

10. The process according to claim 9, wherein the purification solvent is ethanol.

11. The process according to claim 10, wherein the resveratrol concentration of the solution formed in step (e) is in the region of from about 30 to about 50 g/L.

12. The process according to claim 3, wherein the amount of carbon to which the solution formed in step (e) or step i) is contacted will be from about 1.5 kg to about 2 kg per kg of resveratrol.

13. The process according to claim 3, wherein the solution formed in step (e) or step i) is contacted 3 times with 0.5 kg of carbon per kg of resveratrol.

14. The process according to claim 1, wherein crystallisation in step (g) is achieved by decreasing the concentration of the solvent solution to about 40% to about 15% by volume.

15. The process according to claim 1, wherein the precipitated crude resveratrol obtained in step (d) is subjected to pre-crystallisation before being passed to step (e), the pre-crystallisation comprising:
   (x) dissolving the crude resveratrol recovered in step (d) in a first solvent; and
   (y) crystallizing the resveratrol out of the first solvent, said resveratrol having a lower concentration of dihydroresveratrol impurities than present in the precipitated crude resveratrol.

16. The process according to claim 15, wherein the first solvent is the same or different to the purification solvent.

17. The process according to claim 16, wherein the first solvent is selected from methanol, ethanol, propanol, acetone, ethyl acetate, and tetrahydrofuran.

18. The process according to claim 17, wherein the first solvent is ethanol.

19. The process according to claim 18, wherein the ethanol concentration is about 65% to about 80% by volume.

20. The process according to claim 18, wherein the ethanol is mixed at a temperature of about 50° C. to about 80° C.

21. The process according to claim 15, wherein crystallisation in step (y) is achieved by decreasing the concentration of the solvent solution to about 40% to about 15% by volume.

22. The process according to claim 15, wherein steps (x) and (y) are repeated.

23. A composition comprising at least about 70 wt % resveratrol, about 10 to about 5000 mg/kg dihydroresveratrol, and about 10 to about 5000 mg/kg pinosylvin, wherein the composition further comprises bisnoryangonin at a maximum concentration of about 5000 mg/kg as measured by dry weight ratio to resveratrol and wherein the composition is free of emodin.

24. The composition according to claim 23, wherein the composition has about 2 wt % or less water.

25. The composition according to claim 23, wherein the compound has a yellowness index of about 40 to about 5 or less.

26. The composition according to claim 23, wherein the compound has a whiteness index of about −50 or less to about 100.

27. The composition according to claim 23, wherein the composition is dissolved or suspended in a solvent.

* * * * *